United States Patent [19]
Pope et al.

[11] 3,971,362
[45] July 27, 1976

[54] MINIATURE INGESTIBLE TELEMETER DEVICES TO MEASURE DEEP-BODY TEMPERATURE

[75] Inventors: Jack M. Pope; Thomas B. Fryer, both of Saratoga, Calif.

[73] Assignee: The United States of America as represented by the Administrator of the National Aeronautics and Space Administration, Washington, D.C.

[22] Filed: Oct. 27, 1972

[21] Appl. No.: 301,418

[52] U.S. Cl. .............................. 128/2 P; 128/2 H; 128/2.1 A
[51] Int. Cl.² .......................................... A61B 5/07
[58] Field of Search ........ 128/2 H, 2 P, 2 R, 2.1 A, 128/2.1 R

[56] References Cited
UNITED STATES PATENTS

| | | | |
|---|---|---|---|
| 3,218,638 | 11/1965 | Honig | 128/2 P |
| 3,274,994 | 9/1966 | Sturm | 128/2 H |
| 3,453,546 | 7/1969 | Fryer | 128/2.1 A |
| 3,465,103 | 9/1969 | Lynch | 128/2.1 A |
| 3,719,183 | 3/1973 | Schwartz | 128/2 P |

*Primary Examiner*—William E. Kamm
*Attorney, Agent, or Firm*—Darrell G. Brekke; Armand G. Morin; John R. Manning

[57] ABSTRACT

A miniature, ingestible and encapsulated telemeter device for transmitting information relating to deep-body temperature of a subject comprising a battery source of power, and a free running multivibrator circuit having fixed biasing means connected to oscillator having a predetermined resonant frequency. A thermistor having a negative temperature coefficient of resistance is connected to the battery and the fixed biasing means and is operative to vary the output frequency of the multivibrator circuit in proportion to the temperature of the thermistor, the oscillator being pulsed into alernate states of conduction and non-conduction at the output frequency of the multivibrator to produce an output consisting of bursts of energy at the predetermined resonant frequency, preferably in the range 88 – 108 MHz. The time interval between successive bursts is proportionate to the deep-body temperature of the subject, and the thermistor having a very high resistance below a predetermined low temperature to cause inactivation of the multivibrator circuit and thereby only insignificant battery drain during refrigerated storage. A radiating inductor is connected to the output of the oscillator to transmit the bursts to a receiver.

8 Claims, 1 Drawing Figure

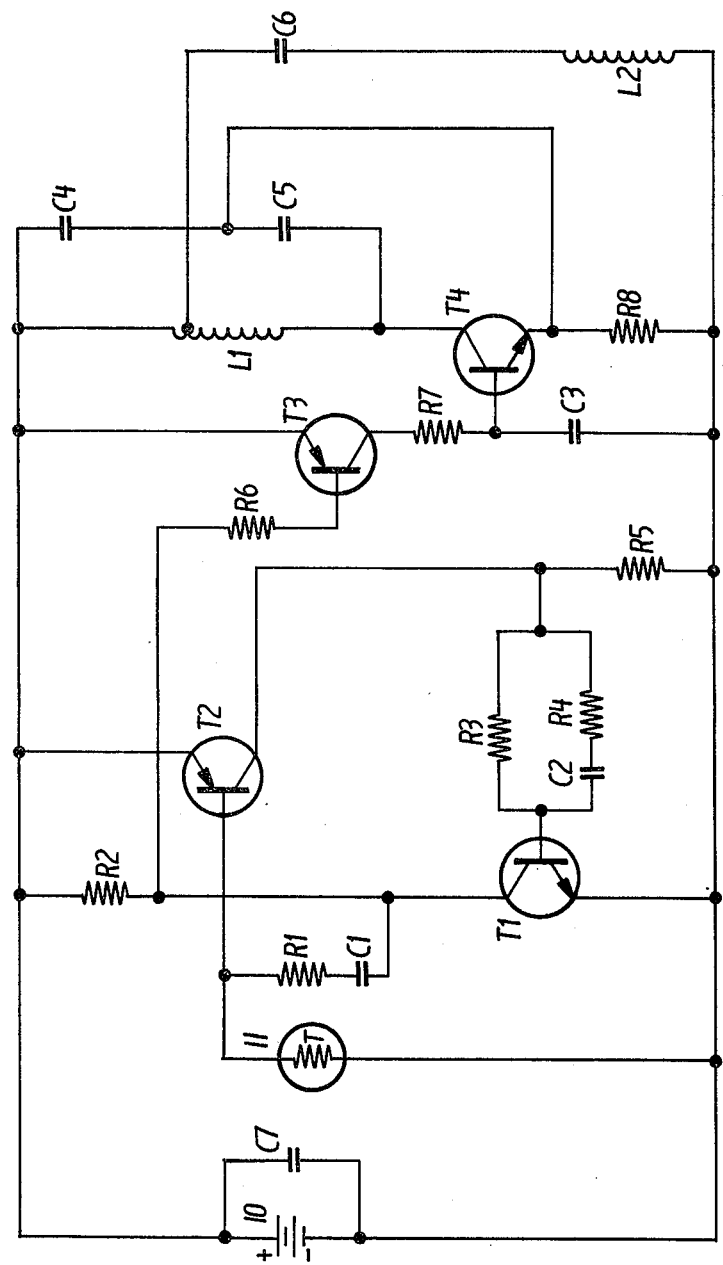

MINIATURE INGESTIBLE TELEMETER DEVICES TO MEASURE DEEP-BODY TEMPERATURE

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

The invention relates to a telemetry device comprising a pill-size ingestible transmitter to obtain deep-body temperature measurements of a human or other subject. It has particular utility in the medical field wherein deep-body temperatures provide an indication of general health.

2. Description of the Prior Art

In the past, deep-body temperature has been measured by hard-wired thermistor ear-probes that must be fitted to the subject's ear in intimate contact with the ear drum. This places the subject in constant discomfort. Thus, U.S. Pat. No. 3,274,994, Sturm, discloses a transmitter inserted into the patient's ear comprising a multivibrator controlled by a thermistor, wherein the multivibrator is activated when a predetermined temperature is reached.

Ingestible transmitters that were first developed were primarily blocking-oscillator telemetry devices using a single transistor as the active element. These devices are simple, but their long-term stability is rather poor and their transmission distances are quite limited. More complicated, stable and accurate transmitter units were later developed for long-term implant. However, these units are large and expensive.

The life of battery-powered telemeters is dependent on the size of the battery, and a large battery cannot be used if the telemeter is to be ingested. A typical battery for ingestible use has a life rating of approximately 16mAH and cannot be remotely controlled. Therefore they constantly draw current from the time the telemeter device is constructed and imbedded in a capsule for ingestion, and must be used immediately if they are to have a practicable period of use.

Passive devices are also known in the art. U.S. Pat. No. 3,229,684, Nagumo et al., discloses a passive telemetering device for physiological measurements which may include a Colpitts oscillator. A thermistor is utilized to vary the time constant variation of a base circuit to affect the oscillating frequency of the transmitter, dependent upon the temperature of the thermistor. Power is supplied to the device by electromagnetic induction from an external source. U.S. Pat. No. 3,407,363, Kaiser et al., also discloses an external power source for a passive implantable FM transmitter, as does U.S. Pat. No. 3,231,834, Watanabe, which relates to a passive telemetering system wherein the transponder response time is proportional to the measured variable.

SUMMARY OF INVENTION

This invention provides a pill-size ingestible active transmitter unit which is relatively simple and inexpensive. The unit may be refrigerated for storage, and in this quiescent state draws an insignificant amount of current from the battery. It is thus not necessary to immediately use the unit after construction thereof.

The unit is imbedded in a capsule for ingestion by the subject. The circuitry includes a small battery connected to energize a multivibrator, buffer amplifier, oscillator and radiating inductor. The frequency of the multivibrator circuit output is determined by the temperature of a thermistor which is correspondingly determined by body temperature of the surrounding ambience. The thermistor has a very high resistance when refrigerated and is connected to the battery and the biasing circuit of the multivibrator to cause the unit to draw an insignificant amount of current when refrigerated.

When in use, the temperature of the thermistor determines the operating frequency of the multivibrator, which pulses the oscillator causing it to emit bursts of energy at the frequency of operation of the multivibrator, the time interval between successive bursts being proportionate to the thermistor temperature. The energy bursts are applied to a radiating inductor to provide a corresponding electromagnetic field for transmission to the receiver.

A buffer amplifier may be connected between the multivibrator and the oscillator to minimize any frequency modulation of the oscillator which might otherwise produce an erroneous temperature indication. The oscillator preferably operates in the 88 to 108 MHz band in order that commercially available FM receivers may be utilized.

BRIEF DESCRIPTION OF THE DRAWINGS

The FIGURE is an electrical schematic diagram of the pill-size, ingestible transmitter according to the invention.

DETAILED DESCRIPTION OF THE INVENTION

The FIGURE shows a free running multivibrator including complementary transistors T1 and T2, which periodically conduct to produce an output having a frequency which depends upon their biasing conditions. Transistor T1 is an NPN transistor with its collector being connected through load resistor R2 to the positive supply terminal of internal battery power supply 10, and its emitter being connected to the negative supply terminal thereof. Transistor T2 is a PNP transistor, with its emitter being connected to the positive supply terminal, and its collector being connected through load resistor R5 to the negative supply terminal. The oscillator is basically a two-stage R-C coupled amplifier with appropriate feedback connections therebetween. Resistor R3 is connected in parallel with the series connection of resistor R4 and capacitor C2, to couple the output of the stage comprising transistor T2 to the base input of transistor T1. The output of the stage comprising transistor T1 is coupled to the base input of transistor T2 through the series connection of resistor R1 and capacitor C1. The operation of the free running oscillator so far described is conventional and is therefore not detailed herein. The output frequency depends upon the biasing elements connected therebetween, and specifically resistors R1, R2, and R4, and capacitors C1 and C2.

Thermistor 11 is, however, connected between the series connection of base of transistor T2 and resistor R1, and the negative supply terminal. It has a negative temperature coefficient and, at a temperature measured at 25°C., a very high resistance of approximately 6 megohms. As the temperature of thermistor 11 increases, its resistance decreases by a proportionate amount which causes a corresponding change in the biasing condition of the multivibrator circuit and consequently the output frequency thereof, as explained hereafter.

In order to drive transistor T2 into conduction, a sufficiently negative signal must be applied to its base. If the resistance of thermistor 11 is sufficiently high, due to a low enough temperature, a sufficiently negative signal will not be applied to the base of transistor T2 and it will not be driven into conduction. As the temperature of thermistor 11 increases, its resistance decreases, causing the base of T2 to become more negative with respect to its emitter and driving transistor T2 into conduction. By complementary multivibrator action, transistor T2 then drives transistor T1 into conduction which causes transistor T2 to conduct even more heavily. This regenerative action continues until there is no further increase in conduction in either transistors T1 or T2. Capacitor C1 then begins to charge through R1, R2 and thermistor 11 until it is charged positive enough to cause transistor T2 to cease conduction. This causes transistor T1 to also cease conduction. Capacitor C1 then starts discharging through R1 and thermistor 11 until the base of T2 becomes negative enough to drive transistor T2 into conduction again. Regenerative action causes the cycle to repeat. Since the discharge path of capacitor C1 includes thermistor 11, the lower its resistance value, the faster the discharge rate of capacitor C1, the faster the discharge rate of capacitor C1, the faster the rate at which transistors T1 and T2 are driven into conduction, and thus the higher the multivibrator frequency. Capacitor C2 and R4 control the conduction time of transistors T1 and T2 while R3 limits the base current of transistor T1.

The multivibrator output is applied to a buffer amplifier comprising PNP transistor T3, through the connection of resistor R6 to the base of transistor T3. The buffer amplifier functions to prevent frequency modulation of the oscillator which might otherwise produce an erroneous temperature indication. The buffer amplifier output is connected to a conventional Colpitts oscillator comprising transistor NPN T4, inductor L1, capacitors C4 and C5, and resistor R8. The Colpitts oscillator is tuned to resonate within the radio frequency range 88 through 108 MHz, in order that conventional FM receivers may be employed to receive the transmitted information. The tuned section of the oscillator comprises tapped inductor L1, and capacitors C4 and C5. Inductor L1 is tapped to provide appropriate impedance matching for radio frequency radiating element L2, connected to the output of the oscillator through DC decoupling capacitor C6, and which transmits the RF signals to an FM receiver.

The oscillator is alternately activated and deactivated at the output frequency of the multivibrator in response to the alternate positive and negative output signals therefrom. The oscillator thus periodically emits bursts of RF energy, with the time interval between bursts being inversely proportional to the temperature of the thermistor. These bursts are applied to the radiating inductor L2 for transmission to the receiver.

The described temperature telemeter comprises an active circuit which has proven accurate to ±0.1°C. from 35°C. to 45°C. The complete device including battery, thermistor controlled multivibrator circuit, buffer amplifier, oscillator, and radiating inductor comprises a miniature unit which may be fitted into a size zero (0) gelatin capsule (approximately 10 mm. in length and 5 mm. in diameter), and then sealed with vinyl-acetate-beeswax and two coatings of silicone rubber. The unit is easily ingestible and is capable of being held by the subject for approximately 35 hours, depending upon diet and activity. Completed units have been tested by immersion for 35 hours in a hydrochloric acid solution of pH 1 at 45°C. to insure the integrity of the coatings which prevent the gelatin capsule from dissolving.

Nominal current drain from the battery at body temperature is 25 microamperes, and the operating life of the encapsulated device is approximately 600 hours. The current drain of encapsulated units can be reduced to negligible values by storage at approximately 0°C., thereby extending the storage time indefinitely. Also the transmitter does not require critical-tolerance parts.

Capacitor C7, capacitor C3 and resistor R7 provide conventional functions and are therefore not described herein. It should be evident that the types of transistors shown and described may be changed, and that an oscillator other than a Colpitts oscillator may be used without departing from the scope of the invention.

I claim:

1. A miniature, ingestible telemeter device for transmitting information relating to deep-body temperature of a subject comprising:
    a free-running multivibrator having complementary transistors;
    an r-f oscillator having a predetermined resonant frequency, said oscillator including an inductor for radiating r-f energy;
    a buffer amplifier coupled between said multivibrator and said oscillator;
    a battery connected to said multivibrator, said buffer amplifier, and said oscillator;
    said free-running multivibrator having temperature-sensitive circuit means for turning on and off said multivibrator and controlling its output pulse frequency when in the on state, said temperature-sensitive circuit means comprising an R-C circuit, said R-C circuit being connected to said battery and to both of said complementary transistors, said R-C circuit including a thermistor;
    means in said multivibrator for turning on said buffer amplifier when said complementary transistors are conducting;
    means in said buffer amplifier for turning on said oscillator when said buffer amplifier is on;
    said multivibrator, said buffer amplifier and said r-f oscillator being in an off state and drawing an insignificant current from said battery when said thermistor is subjected to or below a predetermined temperature which is below the deep-body temperature of the subject ingesting said telemeter device, said free-running multivibrator, said buffer amplifier, and said r-f oscillator being in an on state whenever said thermistor is exposed to a temperature above said predetermined temperature, the output frequency of said multivibrator being proportional to the temperature of said thermistor, said oscillator generating bursts of r-f energy at the output frequency of said multivibrator, the period between successive bursts being inversely proportional to the temperature of said thermistor.

2. A telemeter device as claimed in claim 1 wherein said free-running multivibrator comprises a PNP transistor with a base, collector and emitter, a NPN transistor with a base, collector and emitter, a first resistor and a first capacitor connected in series between said base of said PNP transistor and said collector of said NPN transistor, a second resistor connected between said emitter of said PNP transistor and said collector of said NPN transistor, said thermistor connected between said base of said PNP transistor and said emitter of said NPN transistor, a third resistor connected between said collector of said PNP transistor and said emitter of said NPN transistor, a fourth resistor connected between said base of said NPN transistor and said collector of said PNP transistor, and a fifth resistor and a second capacitor connected in series between said base of said NPN transistor and said collector of said PNP transistor;

the terminals of said battery being connected to said emitter of said PNP transistor and to said emitter of said NPN transistor, respectively, and the input of said buffer amplifier being connected to said collector of said NPN transistor.

3. A telemeter device as claimed in claim 2 wherein said predetermined temperature is 0°C.

4. A telemeter device as claimed in claim 3 wherein the resistance of said thermistor is approximately six megohms at 25°C.

5. A telemeter device as claimed in claim 4 wherein the current drain on said battery during said on state is approximately 25 microamperes.

6. A telemeter device as claimed in claim 1 wherein said predetermined temperature is 0°C.

7. A telemeter device as claimed in claim 6 wherein the resistance of said thermistor is approximately six megohms at at 25°C.

8. A telemeter device as claimed in claim 7 wherein the current drain on said battery during said on state is approximately 25 microamperes.

* * * * *